United States Patent [19]

Friour et al.

[11] Patent Number: 4,865,965

[45] Date of Patent: Sep. 12, 1989

[54] LIGHT SENSITIVE EMULSION AND ELEMENT CONTAINING A CYCLIC ETHER COMPOUND AND PROCESS FOR USING SAME

[75] Inventors: Gerard Friour, Chalon, France; Arthur H. Herz, Rochester, N.Y.; Christian Paris, Chatenoy LeRoyal; Marcel Riveccie, Chagny, both of France

[73] Assignee: Eastman Kodak Company, Rochester, N.Y.

[21] Appl. No.: 194,067

[22] Filed: May 12, 1988

[30] Foreign Application Priority Data

Jun. 12, 1987 [FR] France ............................... 87 08260

[51] Int. Cl.[4] ................................................ G03C 1/34
[52] U.S. Cl. .................................... 430/569; 430/600; 430/603; 430/611; 430/614
[58] Field of Search ............... 430/569, 600, 603, 611, 430/614, 567

[56] References Cited

U.S. PATENT DOCUMENTS

| | | | |
|---|---|---|---|
| 3,062,646 | 11/1962 | Daun et al. | 430/446 |
| 3,271,157 | 9/1966 | McBride | 430/599 |
| 3,767,413 | 10/1973 | Miller | 430/569 |
| 4,276,374 | 6/1981 | Mifune et al. | 430/611 |

FOREIGN PATENT DOCUMENTS 85430 7/1978 Japan .

*Primary Examiner*—Paul R. Michl
*Assistant Examiner*—Janet C. Baxter
*Attorney, Agent, or Firm*—Thomas F. Kirchoff

[57] ABSTRACT

This invention is directed to a light sensitive silver halide emulsion comprising a cyclic ether compound having an acid function and to an element containing such emulsion and to a process for using same. The compound comprises, in the cyclic ring, at least two atoms from the group consisting of sulfur and selenium, each of which atoms being separated from one another by a chain of at least two carbon atoms. Such compound acts as a solvent and as a growth modifying agent for silver halide grains. Also described is a process for modifying the growth of silver halide grains.

35 Claims, No Drawings

LIGHT SENSITIVE EMULSION AND ELEMENT CONTAINING A CYCLIC ETHER COMPOUND AND PROCESS FOR USING SAME

This invention relates to a light sensitive silver halide emulsion which contains a cyclic ether compound. More particularly, this invention relates to a light sensitive emulsion and to an element containing such an emulsion wherein the cyclic ether compound comprises an acid function, and to a process for using same.

Whenever the term "cyclic ether" compound is used herein it refers to what may also be called a "macroheterocyclic" compound. Such compounds include ether type linkages which have at least two atoms selected from the group consisting of sulfur and selenium.

Published art shows that addition of thioether compounds to various stages of silver halide manufacture has the effect of imparting improvements to silver halide properties. For example, U.S. Pat. Nos. 3,062,646 and 3,271,157 disclose macrocyclic thioether compounds which are described as being useful as sensitizers and as solvents for silver halide. These compounds may comprise from 1 to 4 sulfur atoms and from 0 to 4 oxygen atoms in the cyclic ring. However, as is shown below by comparative data, compounds of this type cause fog on storage of the emulsions prior to use and therefore are unsatisfactory for commercial utilization.

Accordingly, the object of this invention is to provide compounds capable of modification of silver halide emulsions during manufacture without causing objectionable increase in fog formation during storage prior to use.

The present invention provides a light sensitive silver halide emulsion comprising a cyclic ether compound having one of the structural formulae:

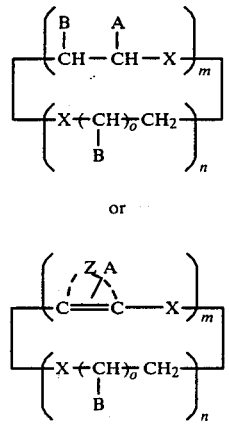

in which formulae

A is $-(L)_p-DR$;

L is a hydrocarbon chain, which can be straight or branched interrupted or substituted by nitrogen, oxygen, sulfur or a carbonyl (C=O) containing group;

D is an acid function;

R is hydrogen, an inorganic cation, ammonium or substituted ammonium, or an organic cation;

each B is independently hydrogen or is as defined for A;

each X is indepdendently a Group VI atom which is sulfur, selenium or oxygen;

m is 1 or 2;

n is 3 to 6;

o is 1 or 2;

each p is indepdendently 0, 1 or 2; and

Z is the atoms necessary to complete an aromatic carbocyclic or an aromatic heterocyclic ring, with the proviso that there are at least 2 sulfur or selenium atoms in the the ring, which atoms are separated from one another by an alkylene chain having at least two carbon atoms.

The hydrocarbon chain represented by L, when present, can comprise from 1 to 5 carbon atoms. These carbon atoms can be in a continuous chain or they can be interrupted. Examples of interrupted chains include $-CH_2-S-CH_2-$, $-CH_2-O-CH_2-$, $-CH_2-N(R)-CH_2$ or

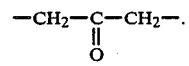

R can be hydrogen or an alkyl group having from 1 to 5 carbon atoms.

The D substituent is referred to herein as an "acid function" and includes, but is not limited to, the OH portion of oxygen acids such as carboxylic ($-COOH$), sulfinic ($-SO_2H$), sulfonic ($-SO_3H$) and hydroxamic ($CO-NHOH$) and the NH portion of nitrogen acids such as for example sulfonamides ($-SO_2NH-$).

Inorganic and organic salts of these groups are equally as useful as are the free acids.

A preferred acidic group is carboxylic, including carboxylate ions derived from salts thereof.

At least one D substituent must be present on the cyclic ether compounds described herein. Additional D substituents are possible.

It is the acid function, in combination with the ether ring structure, which has been found to impart a superior combination of silver halide grain ripening and fog reduction properties to the cyclic ether compounds described herein.

Aromatic carbocyclic rings which can be completed by Z include those having from 6 to 10 ring carbon atoms, including, for example benzene and naphthalene. Aromatic heterocyclic rings completed by Z include those having from 5 to 10 ring atoms. In addition to carbon, the heteroatoms can include at least one of nitrogen, oxygen and sulfur atoms.

As noted in the formulae above, each sulfur, selenium or oxygen atom in the cyclic ether structure is separated from other sulfur, selenium or oxygen atoms by the carbon atoms of an alkylene unit. Successive alkylene units, each including a Group VI atom as defined, are linked together forming a cyclic structure having from about 12 to about 30 ring atoms, preferably from about 15 to about 21 ring atoms. Included within the cyclic structure are from 4 to 8 Group VI atoms which are sulfur, selenim or oxygen, at least 2 of which are sulfur or selenium. Preferably, the ring comprises 5 to 7 atoms which are sulfur, selenium or oxygen.

This invention also provides a light sensitive element comprising a support having thereon a silver halide emulsion layer, said element also comprising a cyclic ether compound as described above. When the cyclic ether compound is incorporated in a silver halide emulsion as a ripening agent the advantages obtained with this invention can be realized without experiencing objectionable levels of fog.

Particular compounds falling within the disclosure of this invention include the following:
Compound 1
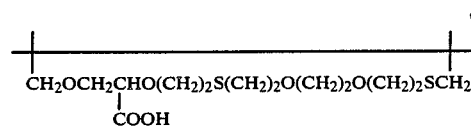
Compound 2
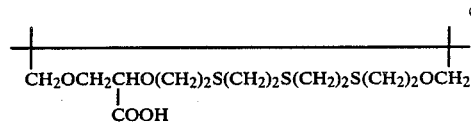
Compound 3
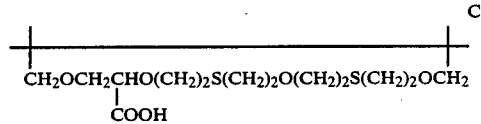
Compound 4
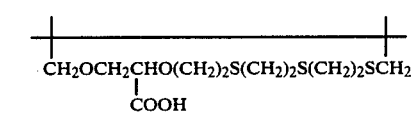
Compound 5
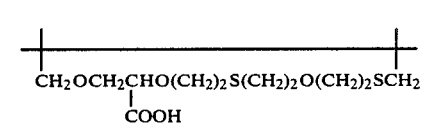
Compound 6
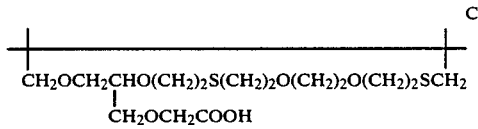
Compound 7
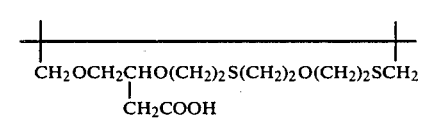
Compound 8
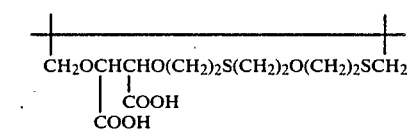
Compound 9
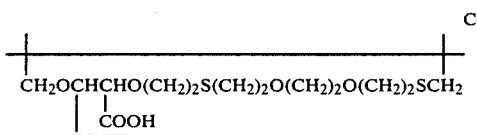
Compound 10
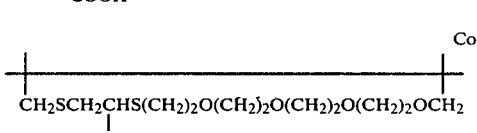
Compound 11
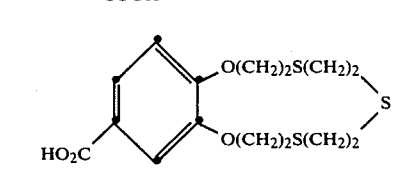
Compound 12
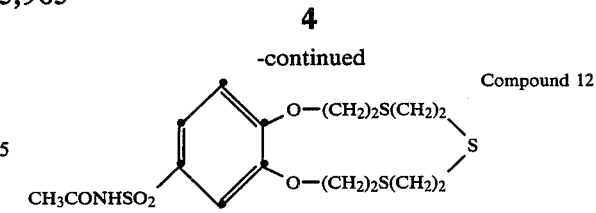
Compound 13
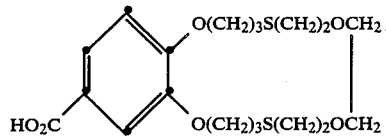
Compound 14
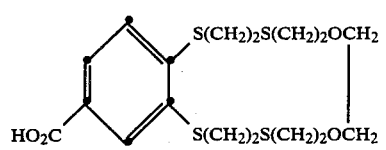
Compound 15
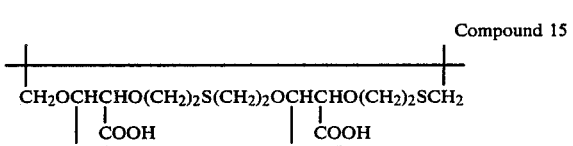
Compound 16
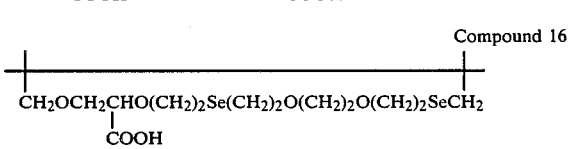
Compound 17
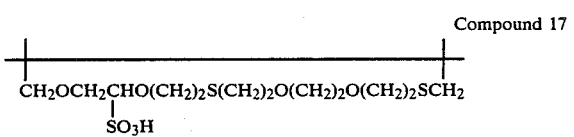
Compound 18
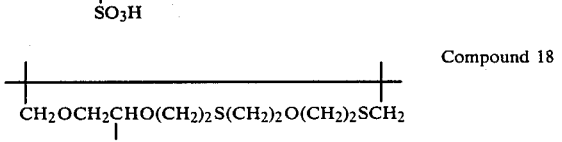
Compound 19
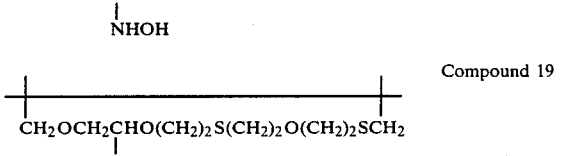
Compound 20
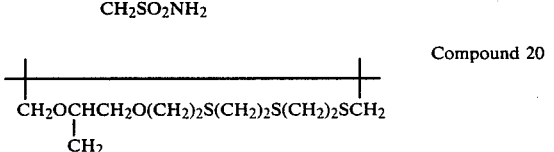
Compound 21

Compound 22

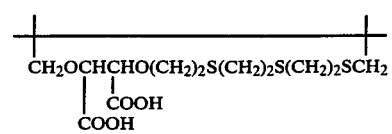

Compound 23

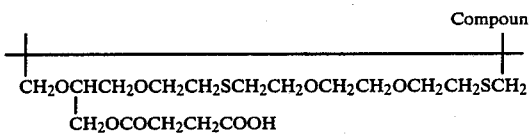

Compound 24

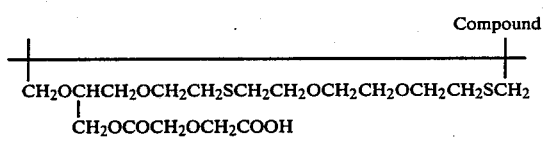

Compound 25

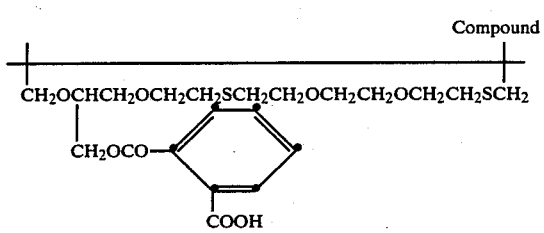

References which provide instructions for the preparation of macrocyclic compounds include "Synthetic Multidentate Macrocyclic Compounds", R. Izatt and J. Christensen, Academic Press, New York, 1978 and "The Chemistry of Ethers, Crown Ethers and Their Sulfur Analogues", ed. S. Patai, John Wiley & Sons, New York, 1980. Introduction of an acid function group on a macrocyclic ether molecule can be accomplished by a multistep synthesis. For example, Compound 1, as shown above, is prepared by following a multiple step synthetic route, the first five steps of which are disclosed by B. Czech et al in Organic Preparation and Procedures, Inc., 15, 29 (1983). The preparation is as follows:

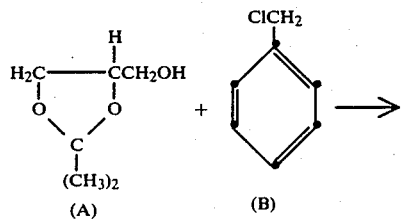

(A)    (B)    (1)

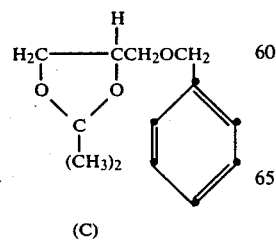

(C)

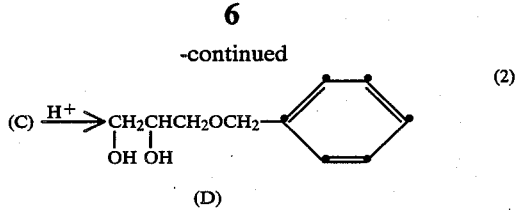   (2)

(D)

   (3)

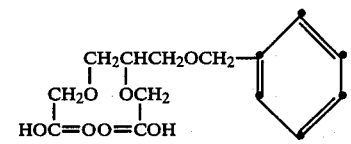

(E)

   (4)

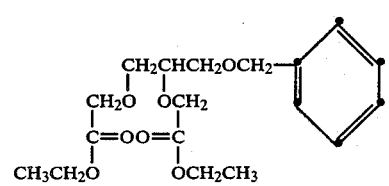

(F)

   (5)

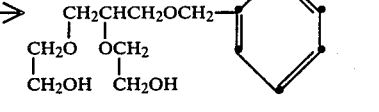

(G)

   (6)

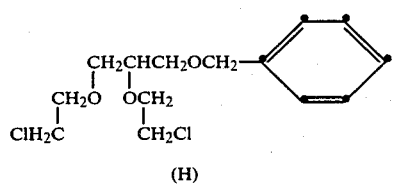

(H)

   (7)

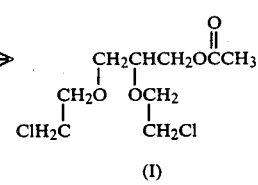

(I)

   (8)

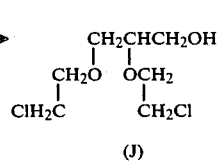

(J)

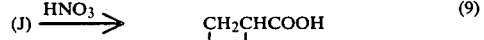   (9)

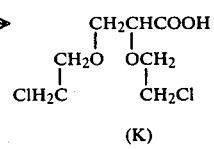

(K)

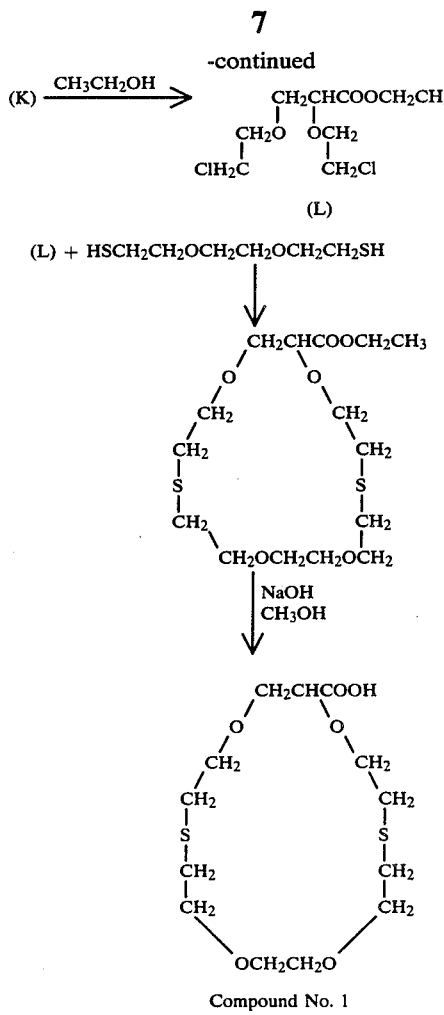

Compound No. 1

Intermediate Compound G, shown above in Step 5 is used to prepare intermediate Compound H as follows:

At 45° C., under a nitrogen atmosphere, 26.2 g (0.22 mol) of $SOCl_2$ is added slowly, over 15 minutes, to a stirred solution of 27 g (0.1 mol) of Compound G in 20 l of dry pyridine.

After the addition, the mixture is heated for 10 minutes at 60°–65° C. and then cooled.

Excess $SOCl_2$ is destroyed by addition of 50 ml of water. Then the mixture is extracted by $3 \times 100$ ml of $CH_2Cl_2$. The combined organic layers are dried ($MgSO_4$) and solvents are eliminated under reduced pressure. Intermediate Compound H is obtained with a yield of 76%.

Intermediate Compound H is utilized in the preparation of Compound I:

30.6 g of Intermediate Compound H are dissolved in 200 ml of acetic acid, 0.5 g of Pd/C 10% and 1 ml $HClO_4$ are added.

The compound is reduced under hydrogen pressure (20 psi) at 50° C. during 10 hours with two more additions of 0.5 g of Pd/C.

After filtration the acetic acid is eliminated under reduced pressure, the crude product is dissolved in 200 ml $CH_2Cl_2$ then washed twice with 100 ml $H_2O$. The organic layer is dried ($MgSO_4$) and the solvent is eliminated under reduced pressure to yield Intermediate Compound I (70% yield).

Intermediate Compound I is converted to Compound J by the following procedure: 10.4 g (0.04 mol) of compound I are stirred 1 hour at room temperature with 8.8 g (0.06 mol) of $K_2CO_3$ in 100 ml $CH_3OH$ and 50 ml $H_2O$.

Solvents are eliminated under reduced pressure and the crude product is diluted with 100 ml acidified water then extracted with $3 \times 100$ ml $CH_2Cl_2$. The combined organic layers are dried ($MgSO_4$) and solvents eliminated under reduced pressure. Compound J is obtained with a yield of 89%.

Intermediate Compound J is oxidized to Compound K by the following procedure: 10.85 g (0.05 mol) of Compound J are added over a 10 minute period to $HNO_3$ (d=1.42) at room temperature. During addition, the temperature rises and a violent reaction starts at about 45° C. with emission of $NO_2$. Afer 1 hour at room temperature 50 ml of water are added to the reaction mixture which is then extracted with $3 \times 100$ ml $CH_2Cl_2$ and $2 \times 100$ ml diethylether.

The combined organic layers are dried ($MgSO_4$) and solvents eliminated under reduced pressure. The residue is dissolved in 50 l ml $H_2O$ containing 7.6 g of $K_2CO_3$ then extracted twice with 100 ml of diethyl ether.

The aqueous layer is acidified with HCl 6N then extractd with $4 \times 100$ ml of diethylether and $2 \times 100$ ml $CH_2Cl_2$.

The combined organic layers are dried ($MgSO_4$) and solvents eliminated. The crude acid Compound K is obtained with a yield of 80% and used as such in preparation of the ethyl ester.

5.7 g (0.0247 mol) of Intermediate Compound K is dissolved in 300 ml of a 1:1 mixture of absolute ethanol and benzene. p-Toluenesulfonic acid (0.5 g) is added and the mixture is refluxed for 6 hours with continuous circulation of the condensing vapors through a Soxhlet thimble containing anhydrous $Na_2SO_4$.

The solvents are removed under reduced pressure and the residue is dissolved in 150 ml $CH_2Cl_2$ and washed with saturated $NaHCO_3$.

The organic layer is dried ($MgSO_4$) and solvents eliminated under reduced pressure. The ethyl ester is obtained as Compound L. The overall yield based on synthesis of intermediate Compounds J and K was 65%.

Intermediate Compound L is reacted with a dithiolether compound to produce the ester derivative of cyclic thioether of Compound I of this invention:

At 80° C., under nitrogen atmosphere and with rapid stirring, a mixture of 3.9 g (0.015 mol) of Intermediate Compound L and 3.0 g (0.0165 mol) of $HS-(CH_2)_2-O-(CH_2)_2-O-(CH_2)_2-SH$, in 75 ml of dry dimethylformamide (DMF) is slowly added over 3.5 hours to 270 ml of dry DMF containing 4.89 g (0.015 mol) of $Cs_2CO_3$ and 0.3 mg of dicyclohexyl 18-CROWN-6.

After cooling and filtration, the DMF is eliminated under reduced pressure. The residue is dissolved in 150 ml $CH_2Cl_2$ and washed twice with 100 ml $H_2O$.

The organic layer is dried ($MgSO_4$) and the solvent eliminated. The ester of Compound 1 is isolated by chromatography on silica gel (Merck 60 H:70 parts) eluent $CH_2Cl_2$).

Hydrolysis of the ester yielded Compound 1:

1.62 g (0.0044 mol) of the ester of Compound 1 is stirred at room temperature during 3 hours in 50 ml of NaOH 1N and 50 ml of $CH_3OH$.

The resulting solution is extracted twice with 50 ml $CH_2Cl_2$. The aqueous layer is acidified, then extracted with 3×100 ml CH$_2$Cl$_2$. The combined organic layers are dried. Elimination of solvent yielded Compound 1 of the invention. Compound 6 can be prepared according to the following synthetic route from Intermediate Compound J of the previous synthesis.

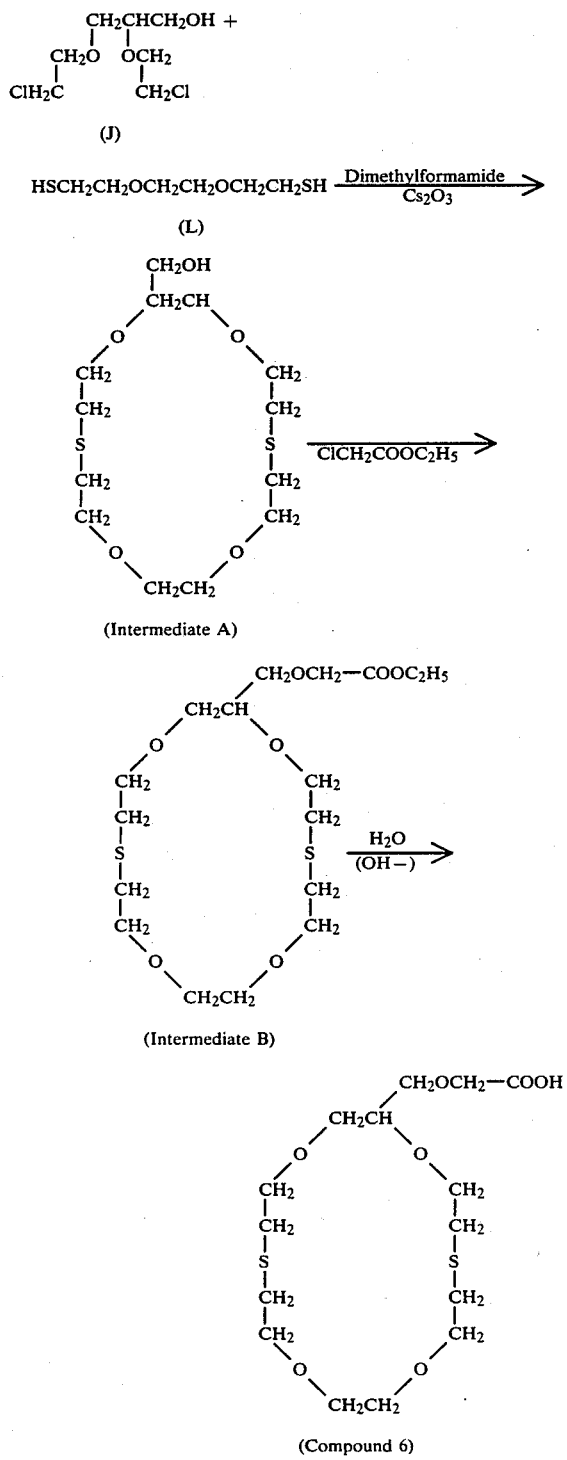

(Compound 6)

A mixture of 450 ml of dimethylformamide (DMF) and 6.52 g (0.020 mol) of Cs$_2$CO$_3$ is heated to 80° C., then a solution containing 3.64 g (0.020 mol) of dithiol compound L and 4.34 g (0.020 mol) of dichloro compound J in 50 ml of DMF is added over a 6 hour period. The heating is maintained at 90° C. for 6 hours. The reaction mixture is filtered and DMF is removed.

The residue is dissolved in 100 ml of CH$_2$Cl$_2$, filtered and the solvent is eliminated. 7.8 g of crude product is obtained. The product is purified by chromatography on SiO$_2$ (Merck 60, 60–200 μm; eluent: CH$_2$Cl$_2$/Methanol 98:2), and dried. 4.56 g of 2-hydroxymethyl-1,4,10,13-tetra-oxa-7,16-dithiacyclooctadecane (Intermediate A) is obtained with a yield of 70%.

In a 100 ml three-necked flask, is placed 5 g (15.3 mmol) of the compound obtained in the previous step, 1.89 g (16.8 mmol) of potassium t-butoxide, and 30 ml of t-butyl alcohol; the mixture is refluxed for 30 minutes. Ethyl chloroacetate is added at once. the mixture is refluxed overnight.

Solvent is eliminated under reduced pressure. The resulting black oil is dissolved in 60 ml of CH$_2$Cl$_2$ then washed with 50 ml of H$_2$O and 5 ml of HCl (10N). The product is washed again with 50 ml of H$_2$O and dried (MgSO$_4$); the solvent is eliminated. 5.89 of crude compound (Intermediate B) is obtained, then purified by chromatrography on SiO$_2$ (Merck 60 μm-Eluent CH$_2$Cl$_2$/Ethanol 99.5:0.5).

A solution containing 3.33 g (7.9 mmol) of the ester (Intermediate B) of the previous step and 18 ml of methanol is prepared in a 100 ml flask. A solution of 3.15 g (79 mmol) of NaOH in 18 ml of H$_2$O is added. The mixture is stirred at room temperature overnight. 12 ml of HCl (10N) is added and the mixture is extracted with 3×50 ml of CH$_2$Cl$_2$. The organic phase is dried and the solvent eliminated.

The crude product obtained is dissolved in 50 ml of NaOH (2N), then washed with 2×50 ml of CH$_2$Cl$_2$. The aqueous phase is acidified with 40 ml of HCl (10N). The solution is extracted with 2×250 ml of CH$_2$Cl$_2$, then dried. The solvent is removed. 2.80 g (92%) of Compound 6 is obtained.

Compounds 20 and 21 can be prepared in the same way, by using appropriate dithiol compounds.

Compound 9 can be prepared according to the following synthetic route. The first five steps are disclosed in the publication of A Anantanarayan, P. J. Dutton, T. M. Fyles et M J. Pitre, J. Org. Chem. 1986 Vol. 51 No. 5 p. 752.5.

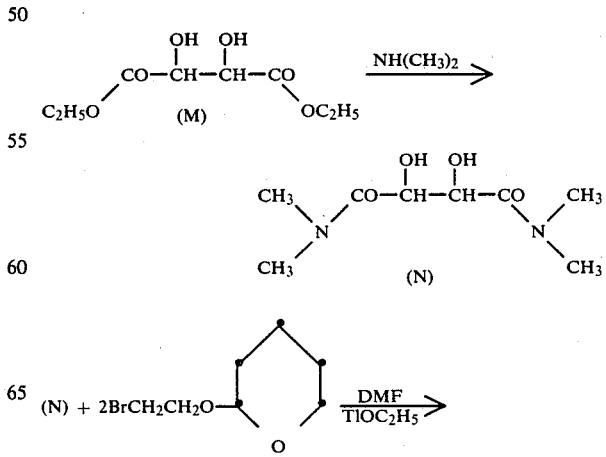

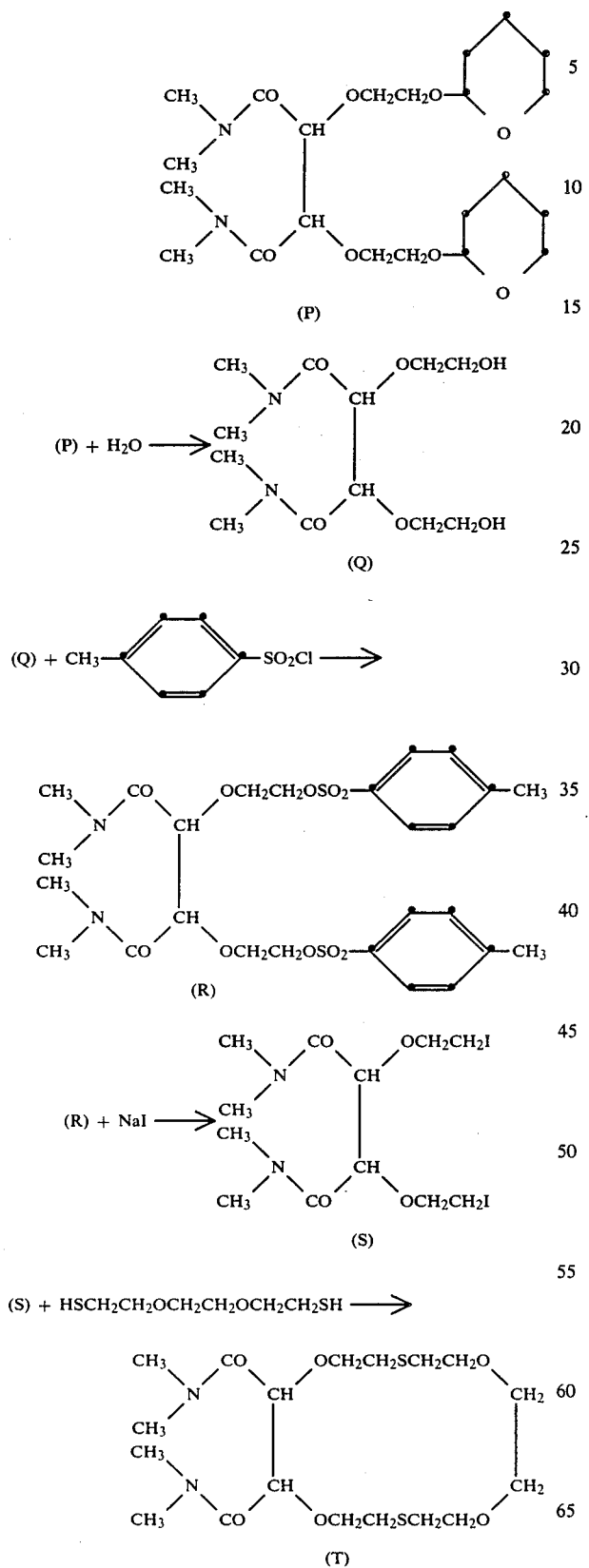

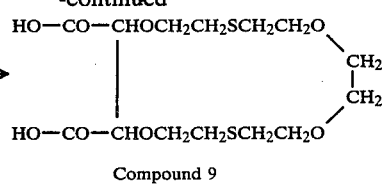

Compound 9

Preparation of intermediate compound N,N,N',N'-tetramethyl-1,4,10,13-tetraoxa-7,16-dithiocyclooctadecane-1,2,-dicarboxamide (Compound T)

In a 2 l, three-necked, round-bottomed flask fitted with a reflux condenser, thermometer, dropping funnel and magnetic stirring is placed, under a nitrogen atmosphere, 6.3 g (19.3 mmol) of cesium carbonate. 900 ml of dry DMF is poured and the mixture is heated to 50° C. Then, a solution of 9.91 g (19.3 mmol) of tetramethyl-bis-(iodoethoxy)-succinamide and 3.5 g (19.3 mmol) of 3,6-dioxa-1,8-dithiaoctane in 100 ml of DMF is slowly added in 6 hours. The mixture is stirred overnight at 50° C., filtered, and DMF is evaporated under reduced pressure. The crude product is purified by chromatography on silica and yielded 1.86 g (22%) of Compound T.

Preparation of Compound 9

In a 50 ml round-bottom flask equipped with a stirring rod and a reflux condenser is placed 1.66 g (3.79 mmol) of the diamide (Compound T), 34.4 ml of $H_2O$ and 3.44 ml of HCl 10N (34.4 mmol). The mixture is heated at 80° C. for 20 hours and cooled down to room temperature.

The mixture is eluted through a column of 150 g of Dowex 50X2-200 resin in the acidic form in order to exchange $(CH_3)_2NH_{2+}$ cations with $H^+$ cations. The eluate is then concentrated to approximately 50 ml on the rotative evaporator under high vacuum at 50° C.

In order to remove chloride anions, a solution of 6.03 g (36.1 mol) of AcOAg in 615 ml of hot water is added to the chlorhydric solution of the dicarboxylic thioether. Silver chloride is eliminated by centrifugation and filtration through an hydrophilic 0.2 µm-filter (Millipore:EG type) to remove last traces of solid. The solution is then concentrated to approximately 50 ml and filtered again as above in order to remove precipitated silver chloride and acetate.

The solution is then passed through a 100 g Dowex 50X2-200 resin in its acidic form to exchange $Ag^+$ cations of the excess AcOAg and the complex with $H^+$ cations. The eluate is concentrated to 50 ml. This solution is free of chloride anions (no precipitate with silver nitrate solution) and free of silver cations (no precipitate with sodium chloride solution). The acetic solution resulting is then evaporated and yielded 0.70 g (48%) of compound 9.

Compound 22 can be prepared in the same way, by using the appropriate dithiol.

Compounds 23, 24 and 25, as well as their homolgues comprising various cyclic thioethers type linkages can be prepared in quantitative yield from intermediate compounds which have an alcohol function. Such intermediate compounds are similar to Intermediate A, described above in the preparation of Compound 6, and have the general formula designated "U":

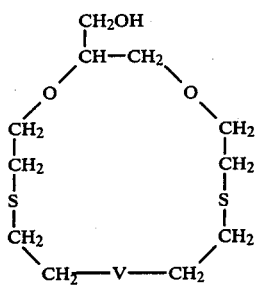
(U)

where V is —OCH$_2$CH$_2$O—, —S— or —O—.

The preparation comprises reacting "U" with an anhydride of the formula:

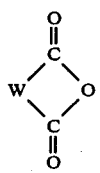

in the presence of triethylamine Compounds 23, 24 and 25 were prepared wherein V was in each instance —OCH$_2$CH$_2$O— and wherein for Compound 23, W was —CH$_2$—CH$_2$; for Compound 24, W was —CH$_2$—O—CH$_2$—; and for Compound 25, W was

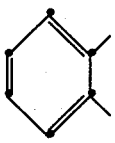

A photographic element of this invention comprises a support, at least one photosensitive silver halide emulsion layer and a cyclic ether compound as described above. The ether compound may be present in the silver halide emulsion layer. However, when it is the function of the cyclic ether compound to act as a solvent for silver halide during development, or subsequent processes, such as silver salt diffusion process, the ether compound may alternatively be located in another hydrophilic layer, such as an intermediate layer, from which it can diffuse during processing into a silver halide emulsion layer.

Incorporation of a cyclic ether compound in a silver halide emulsion layer can be achieved at various steps in the preparation of the emulsion. The preparation of silver halide emulsions is well known and is described, for example, in *Research Disclosure*, Vol. 176, December 1978, Item 17643, paragraphs I and II. The emulsions can be chemically sensitized as described in paragraph III of the same publication. A cyclic ether compound can be incorporated during a ripening step where it will serve to modify the growth of silver halide grains. It can be used by itself or in combination with other ripening agents or growth modifiers or spectral sensitizers, stabilizers, antifoggants and other useful emulsion additives. The ether compound can also be incorporated in the chemical sensitization step, preferably simultaneously with other chemical sensitizing agents. Useful amounts of cyclic ether compound will vary depending upon such factors as the type of emulsion, the particular cyclic ether selected, and the specific effects that are sought. Generally, amounts range from about $5 \times 10^{-6}$ to about $1 \times 10^{-1}$ mol/silver mol, with from about $10^{-4}$ to $10^{-2}$ mol/silver mol being preferred.

Preferably, chemical sensitizing agents employed in combination with cyclic ethers are noble metals such as gold or gold in combination with sulfur or selenium compounds. In comparison to thioether compounds used as co-sensitizing agents according to the prior art, the cyclic ether compounds described herein do not cause undesirable fog increase or loss of spectral sensitivity. This is shown by examples below.

Alternatively, the cyclic ether compounds described herein can be incorporated during the melting step for the silver halide emulsion immediately prior to coating. In this case, the amount of ether compound is preferably from about $1 \times 10^{-4}$ to about $10^{-2}$ mol/silver mol.

When a cyclic ether compound as described herein is incorporated in a hydrophilic colloid layer adjacent to a silver halide emulsion layer, such as in an intermediate layer separating adjacent silver halide emulsion layers, the cyclic ether is preferably coated at a coverge of from about $1 \times 10^{-7}$ to about $1 \times 10^{-5}$ mg/dm$^2$.

When the ether compound is incorporated in a silver halide emulsion layer or in a layer adjacent to a silver halide emulsion layer during the melting stage prior to coating it is believed that the ether compound functions primarily as a silver halide solvent and a development modifying agent rather than as a co-sensitizing agent. Preferably silver halide grains having an aspect ratio higher than 5:1 are used.

In still another alternative, a cyclic ether compound of this invention can be incorporated in a photographic element from a processing solution by incorporating the cyclic ether in the processing solution in an amount of from about $5 \times 10^{-5}$ to abou $1 \times 10^{-3}$ mol/liter. In this alternative the ether compound acts basically as a processing accelerator. However, enhancement of the desired properties of the photographic element results regardless of which manner of action is ascribed to the cyclic ether compound.

This invention also provides a process for the growth modification of silver halide grains which comprises adding, during preparation of said grains or prior to coating thereof on a support, from about $10^{-6}$ to about $10^{-1}$ mol per mol of silver halide, of a cyclic ether compund having one of the structural formulae:

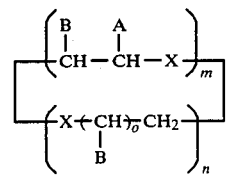

I or

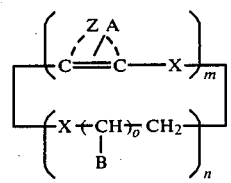

II in which formulae

A is $-(L)_p-DR$;

L is a hydrocarbon chain, which is straight or branched, which can be interrupted or substituted by nitrogen, oxygen, sulfur or a carbonyl (C=O) containing group;

D is an acid function;

R is hydrogen, an inorganic cation, ammonium or substituted ammonium, or an organic cation;

each B is independently hydrogen or is as defined for A;

each X is independently a Group VI atom which is sulfur, selenium or oxygen;

m is 1 or 2;

n is 3 to 6;

o is 1 or 2;

each p is independently 0, 1 or 2; and

Z is the atoms necessary to complete an aromatic carbocyclic or an aromatic heterocyclic ring, with the proviso that there are at least 2 sulfur or selenium atoms in the ether ring, which atoms are separated from one nother by an alkylene chain having at least two carbon atoms.

A preferred concentration of ether compound to achieve growth modification of silver halide is from about $10^{-4}$ to about $10^{-2}$ mol thereof per mol of silver halide.

The silver halide grains can be of any halide composition (e.g., silver bromide, silver bromoiodide, silver chloride, or silver chlorobromoiodide), of any size (e.g., coarse or fine), ahd can be of any regular or irregular shape (e.g., spherical, regular cubic, regular octahedral, cubo-octahedral, or tabular octahedral) known to be useful in photography. Conventional vehicles can be used, such as those described in *Research Disclosure* (RD), Item 17643, cited above, paragraph IX. Silver halides can be spectrally sensitized as described in paragraph IV of the same RD reference.

The improvements of this invention can be applied to black and white photography (including radiography), or, preferably, to color photography, to form silver images and/or dye images by selective dye destruction, formation or physical elimination, as described in paragraph VII of the RD publication noted. Preferred color photographic elements are those that form dye images by means of color developers or dye forming couplers. To use these elements, they can be exposed and processed in any known manner as described in paragraphs XVIII and XIX of the above-mentioned RD reference.

The following examples are presented as further illustrations of the invention.

EXAMPLE 1

Four tabular grain silver bromoiodide emulsions were prepared according to a procedure similar to the one disclosed in Example 3 of U.S. Pat. No. 4,434,226.

One of these emulsions was prepared without an ether compound (Control), another with a thioether of U.S. Pat. No. 3,062,646 (1,10-dithia-4,7,13,16-tetraoxacyclooctadecane (Comparison), the third with Compound 1 as identified above, and the fourth with Compound 4 as identified above.

Each ether compound was added in an amount of $1.69 \times 10^{-4}$ mol/mol Ag in the silver nitrate solution during grain growth.

Average diameter and average thickness of grains, and width variation coefficients were determined on the resulting emulsions.

The following table summarizes the results obtained.

TABLE I

| Ether Compound | Diameter (μm) ECD* | Coefficient Variation | Average Thickness μm | Aspect Ratio |
|---|---|---|---|---|
| Control none | 1.65 | 0.506 | 0.12 | 14:1 |
| Comparison (U.S. Pat. No. 3,062,646) | 1.80 | 0.359 | 0.13 | 14:1 |
| Compound 1 (Invention) | 1.95 | 0.472 | 0.10 | 19.5:1 |
| Compound 4 (Invention) | 1.45 | 0.337 | 0.15 | 9.6:1 |

*ECD = Equivalent circular diameter

These results show that cyclic ethers of this invention influence growth of silver halide grains, including grains having aspect ratios different from those obtained with the prior art thioether compounds.

EXAMPLE 2

Experiments were carried out with 8 mM AgBr dispersed at pH 3, pBr 3 in 0.02% ossein gelatin (isoelectric point 4.9) containing 28 mM $KNO_3$ and 0.3 mM of the ether compound noted in the following table. These emulsions were stirred for 16.5 hrs. at 25° C. Evaluation of subsequently obtained electronmicrographs yielded the following results.

TABLE II

| Sample | Equivalent Circular Diameter, (μm) |
|---|---|
| Control (no thioether) | 0.165 |
| Thioether A* | 0.424 |
| Invention (Compound 1) | 0.664 |

*Thioehter A is the same compound as the Comparison Compound in Example 1, above.

It is apparent that under the given conditions, Compound 1 is an effective ripening agent and increases AgBr particle dimensions more than does the non-acid function containing compound of the prior art.

EXAMPLE 3

The following test is based on a polydispersed, negative-type silver bromoiodide (6 mol % iodide) gelatin emulsion containing 0.15 mmol/mol silver of a disulfoalkyl oxacarbocyanine dye. After addition of the indicated compounds at 40° C., pH 5.8 and pBr 3, the emulsions were coated and conventionally processsed in KODAK Developer D19. Unprocessed coatings were used for the determination of absorptance, A, which is defined by $A = 1 - (R+T)$, where the last terms refer, respectively, to reflectance and transmittance. To test for storage stability, unprocessed coatings were kept at 49° C., 50% relative humdity (RH) for 1 week.

TABLE III

| Part A | |
|---|---|
| Additive 0.3 mmol/mol Ag | Absorptance % A at 555 nm |
| Control (no thioether) | 58.3 |
| Thioether B | 39.0 |
| Compound 4 (Invention) | 49.1 |

| Part B | |
|---|---|
| Additive 3 mmol/mol Ag | Relative Green Speed (Wratten Filters 16 & 61) |
| Control (no thioether) | 100 |
| Thioether A | 23.5 |

TABLE III-continued

| Compound 1 (Invention) | 97 |
| --- | --- |

Part C

| Additive 1 mmol/mol Ag | Relative Green Speed (Wratten Filters 36 & 38A) | 1 Week Storage Fog |
| --- | --- | --- |
| Control (no thioether) | 100 | 0.54 |
| Thioether A | 102 | 0.73 |
| Compound 1 (Invention) | 105 | 0.53 |

Thioether A is the same as the Comparison Compound in Example 1 above. Thioether B, 1,4,7-trithia,10,13-dioxacyclopentadecane, is similar to cyclic compounds described in U.S. Pat. No. 3,271,157.

Part A demonstrates that the intensity of the 555 nm peak, which is associated with the adsorbed carbocyanine dye, is more adversely decreased by Thioether B than by Compound 4, an acid-substituted thioether compound of this invention. Similarly, it is apparent from Part B that spectral sensitization by the carbocyanine dye is barely influenced by an acid-function containing cyclic ether compound as described herein. By contrast, the neutral prior art Compound Thioether A is seen to interfere with spectral sensitization and to induce a drastic speed loss.

From Part C it is apparent that while neither cyclic ether compound initially has any deleterious effect on the emulsion's intrinsic sensitivity, acid-substituted cyclic ether Compound 1, as described herein, is also without deleterious effect on the emulsion's storage stability. This inertness is distinct from the behavior of the prior art thioether which destabilizes the emulsion during storage and enhances formation of fog.

EXAMPLE 4

This example illustrates the improved fog reduction on storage obtained by the acid-function cyclic ether compounds of the present invention.

Three samples of an octahedric AgBrI emulsion were prepared. Before the chemical sensitization step, the following compounds were added:

| Control 1 = none | |
| --- | --- |
| Comparison (a) | 30 mg/mol Ag |
| Invention = Compound 23 | 60 mg/mol Ag |

Comparison (a) 1,10-dithia-4-7,13,16-tetraoxacyclooctadecane of U.S. Pat. No. 3,062,646.

The completed emulsions were tested in an Xray type of processing, then incubated at 50 C, 50% RH, for periods of 2 days, 7 days, 14 days and 24 days. Results are shown in Table IV.

TABLE IV

| Compound | Gross Fog After Indicated Days Incubation | | | | |
| --- | --- | --- | --- | --- | --- |
| | 0 | 2 | 7 | 14 | 24 |
| Control (none) | 0.18 | 0.18 | 0.19 | 0.20 | 0.21 |
| Comparison | 0.18 | 0.18 | 0.19 | 0.23 | 0.29 |
| Compound 23, Invention | 0.18 | 0.18 | 0.18 | 0.20 | 0.21 |

From the results of Table IV, it is apparent that the emulsion containing the Compound of this invention gives no more fog than the emulsion without a thioether compound, and much less fog than the thioether compound of the prior art.

This invention has been described in detail with particular reference to preferred embodiments thereof, but it will be understood that variations and modifications can be effected within the spirit and scope of the invention.

What is claimed is:

1. A light sensitive silver halide emulsion comprising a cyclic ether compound having one of the structural formulae:

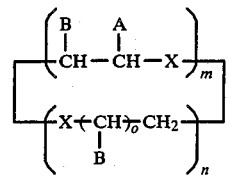

I or

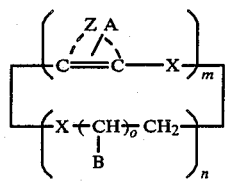

II in which formulae

A is $-(L)_p-DR$;

L is a hydrocarbon chain which can be straight or branched, interrupted or substituted by a nitrogen, oxygen, sulfur or a carbonyl containing group;

D is an acid function;

R is hydrogen, an inorganic cation, ammonium or substituted ammonium, or an organic cation;

each B is independently hydrogen or is as defined for A;

each X is independently a Group VI atom which is sulfur, selenium or oxygen;

m is 1 or 2;

n is 3 to 6;

o is 1 or 2;

each p is independently 0, 1 or 2, and

Z is the atoms necessary to complete an aromatic carbocyclic or an aromatic heterocyclic ring, with the proviso that there are at least 2 sulfur or selenium atoms in the ether ring, which atoms are separated from one another by an alkylene chain having at least two carbon atoms.

2. The emulsion of claim 1 wherein the acid function is a carboxylic, hydroxamic, sulfinic or sulfonic group.

3. The emulsion of claim 1 wherein said cyclic ether compound comprises from about 12 to about 30 atoms in the ring structure.

4. The emulsion of claim 3 wherein said cyclic ether compound comprises from about 15 to about 21 atoms in the ring structure.

5. The emulsion of claim 1 wherein there are from 4 to 8 sulfur, selenium and oxygen atoms in the ring structure.

6. The emulsion of claim 1 wherein B is hydrogen.

7. The emulsion of claim 1 wherein A represents a carboxy group.

8. The emulsion of claim 7 wherein carboxy groups are present on adjacent ring carbon atoms.

9. The emulsion of claim 1 wherein p is 0.

10. The emulsion of claim 1 wherein said cyclic ether compound is present in an amount of from about $5\times10^{-6}$ to about $1\times10^{-1}$ mol thereof per mol of silver halide.

11. The emulsion of claim 10 wherein said ether compound is present in an amount of from about $10^{-4}$ to about $10^{-2}$ mol thereof per mol of silver halide.

12. The emulsion of claim 1 wherein said cyclic ether compound has the structural formula:

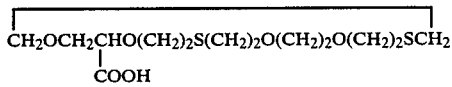

13. The emulsion of claim 1 wherein said cyclic ether compound has the structural formula:

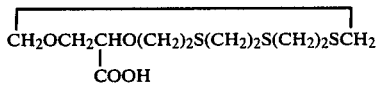

14. The emulsion of claim 1 wherein said cyclic ether compound has the structural formula:

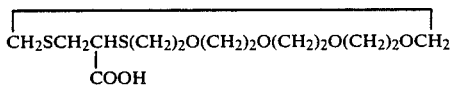

15. The emulsion of claim 1 wherein said cyclic ether compound has the structural formula:

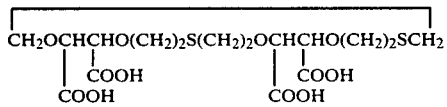

16. The emulsion of claim 1 wherein said cyclic ether compound has the structural formula:

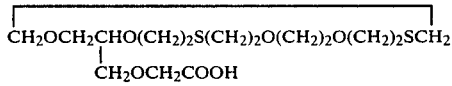

17. A light sensitive silver halide element comprising a support and a silver halide emulsion layer which element also comprises a cyclic ether compound having the structural formulae:

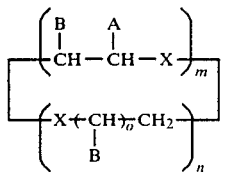

or

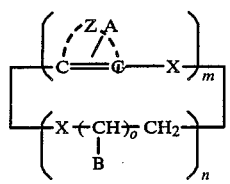

in which formulae

A is $-(L)_p-DR$;

L is a hydrocarbon chain which can be straight or branched, interrupted or substituted by nitrogen, oxygen, sulfur or a carbonyl containing group;

D is an acid function;

R is hydrogen, an inorganic cation, ammonium or substituted ammonium, or an organic cation;

each B is independently hydrogen or is as defined for A;

each X is independently a Group VI atom which is sulfur, selenium or oxygen;

m is 1 or 2;

n is 3 to 6;

o is 1 or 2;

each p is independently 0, 1 or 2, and

Z is the atoms necessary to complete a benzene ring, with the proviso that there are at least 2 sulfur or selenium atoms in the ether ring, which atoms are separated from one another by an alkylene chain having at least two carbon atoms.

18. The element of claim 17 wherein the acid function is a carboxylic, hydroxamic, sulfinic or sulfonic group.

19. The element of claim 17 wherein said cyclic ether compound comprises from about 12 to about 30 atoms in the ring structure.

20. The element of claim 19 wherein said cyclic ether compound comprises from about 15 to about 21 atoms in the ring structure.

21. The element of claim 17 wherein there are from 4 to 8 sulfur, selenium and oxygen atoms in the ring structure.

22. The element of claim 17 wherein B is hydrogen.

23. The element of claim 17 wherein A represents a carboxy group.

24. The element of claim 23 wherein carboxy groups are present on adjacent ring carbon atoms.

25. The element of claim 17 wherein p is 0.

26. The element of claim 17 wherein said ether compound is present in a silver halide emulsion layer.

27. The element of claim 26 wherein the emulsion layer comprises silver halide grains having an aspect ratio higher than 5:1.

28. The element of claim 17 wherein said cyclic ether compound is present in an amount of from about $5\times10^{-6}$ to about $1\times10^{-1}$ mol thereof per mol of silver halide.

29. The element of claim 28 wherein said ether compound is present in an amount of from about $10^{-4}$ to about $10^{-2}$ mol thereof per mol of silver halide.

30. The element of claim 17 wherein said cyclic ether compound has the structural formula:

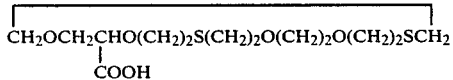

31. The element of claim 17 wherein said cyclic ether compound has the structural formula:

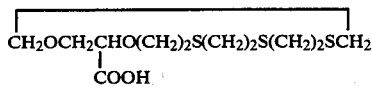

32. The element of claim 17 wherein said cyclic ether compound has the structural formula:

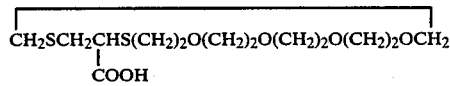

33. The element of claim 17 wherein said cyclic ether compound has the structural formula:

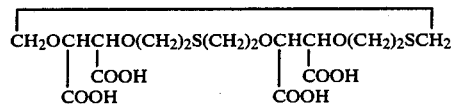

34. The element of claim 17 wherein said cyclic ether compound has the structural formula:

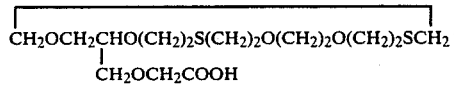

35. In a process for the growth modification of silver halide grains, the improvement which comprises adding, during preparation of said grains or prior to coating thereof on a support, from about $10^{-6}$ to about $10^{-1}$ mol, per mol of silver halide, of a cyclic compound having one of the structural formulae:

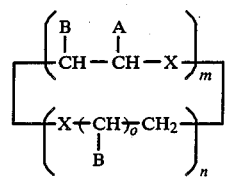

or

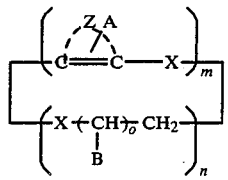

in which formulae
A is $-(L)_p-DR$;
L is a hydrocarbon chain which can be interrupted or substituted by nitrogen, sulfur or a carboxyl group;
D is an acid function;
R is hydrogen, an inorganic cation, ammonium or substituted ammonium, or an organic cation;
B is hydrogen or is as defined for A;
X is a Group VI atom which is sulfur, selenium or oxygen;
m is 1 or 2;
n is 3 to 6;
o is 1 or 2;
each p is independently 0, 1 or 2, and
Z is the atoms necessary to complete a benzene ring, with the proviso that there are at least 2 sulfur or selenium atoms in the ether ring, which atoms are separated from one another by an alkylene chain having at least two carbon atoms.

* * * * *